US005649973A

United States Patent [19]
Tierney et al.

[11] Patent Number: 5,649,973
[45] Date of Patent: Jul. 22, 1997

[54] THERMOTHERAPY METHOD WITH TISSUE COOLING

[75] Inventors: Mark Tierney; Richard diMonda, both of Marietta, Ga.

[73] Assignee: Dornier Medical Systems, Inc., Kennesaw, Ga.

[21] Appl. No.: 561,925

[22] Filed: Nov. 22, 1995

Related U.S. Application Data

[62] Division of Ser. No. 291,336, Aug. 17, 1994, abandoned, which is a continuation of Ser. No. 976,232, Nov. 13, 1992, abandoned.

[51] Int. Cl.$^6$ .................................................... A61F 7/00
[52] U.S. Cl. ........................... 607/101; 607/102; 607/104; 607/105; 607/113; 607/154; 607/156
[58] Field of Search .................................. 607/100, 101, 607/102, 104, 105, 113, 154, 156; 606/192

[56] References Cited

U.S. PATENT DOCUMENTS

| Re. 33,791 | 1/1992 | Carr . |
| 3,460,538 | 8/1969 | Armstrong . |
| 3,977,408 | 8/1976 | MacKew . |
| 4,311,154 | 1/1982 | Sterzer et al. . |
| 4,375,220 | 3/1983 | Matvias . |
| 4,378,806 | 4/1983 | Henley-Cohn . |
| 4,601,296 | 7/1986 | Yerushalni .................. 607/156 |

(List continued on next page.)

FOREIGN PATENT DOCUMENTS

| 0 370 890 A1 | 11/1989 | European Pat. Off. . |
| 24 07 559 C3 | 1/1982 | Germany . |
| 2 045 620 | 3/1980 | United Kingdom . |

OTHER PUBLICATIONS

"Prostatic and Periprostatic Interstitial Temperature Measurements in Patients Treated with Transrectal Thermal Therapy (Local Intracavitary Microwave Hyperthermia)," Steven A. Kaplan et al., The Journal of Urology, vol. 147, pp. 1562–1565 (Jun. 1992).

"Microwave Surgical Treatment of Diseases of Prostate," Harada et al., Urology, Dec. 1985, vol. XXVI, No. 6.

*Primary Examiner*—Angela D. Sykes
*Assistant Examiner*—Rosiland Kearney
*Attorney, Agent, or Firm*—Reinhart, Boerner, Van Deuren, Norris & Reiselbach, s.c.

[57] ABSTRACT

A method for performing thermotherapy treatment of patient prostate tissue, comprising the steps of inserting a thermotherapy probe in a urethral passageway, the probe having a fluid volume containing portion and an energy source inserted therein for generating radiation to heat the patient prostate tissue by the tissue absorbing the radiation; generating a pressurized fluid flow in the probe within the fluid volume containing portion and cooling the energy source by enveloping at least a portion of the energy source to direct the pressurized fluid flow to come into direct contact with and circulate around and over all energy radiating portions of the energy source simultaneously with energy radiation by the energy source, thereby preventing thereby preventing thermal damage to the energy source; and providing an inflatable nondistensible structure as part of the probe inserted into the urethral passageway and inflating the nondistensible structure with the pressurized fluid flow to cool tissue contacting the nondistensible structure simultaneously with energy radiation by the energy source, thereby controlling pain caused by heating localized areas of the tissue contacting the nondistensible structure, and the nondistensible structure upon inflating causing straightening along a longitudinal axis of the treated patient prostate tissue and the straightening enabling greater uniformity and effectiveness of treatment of the prostate tissue.

6 Claims, 6 Drawing Sheets

U.S. PATENT DOCUMENTS

| | | |
|---|---|---|
| 4,612,940 | 9/1986 | Kasevich et al. |
| 4,662,383 | 5/1987 | Sogawa et al. |
| 4,681,122 | 7/1987 | Winters et al. |
| 4,813,429 | 3/1989 | Eshel et al. |
| 4,887,614 | 12/1989 | Shirakami et al. |
| 4,955,377 | 9/1990 | Lennox et al. |
| 4,967,765 | 11/1990 | Turner et al. |
| 4,988,163 | 1/1991 | Cohen et al. |
| 5,007,437 | 4/1991 | Sterzer . |
| 5,025,778 | 6/1991 | Silverstein et al. |
| 5,061,267 | 10/1991 | Zeiher . |
| 5,151,100 | 9/1992 | Abele et al. |
| 5,220,927 | 6/1993 | Astrahan et al. |
| 5,234,004 | 8/1993 | Hascoet et al. .......................... 607/156 |
| 5,295,994 | 3/1994 | Bonutti . |
| 5,330,518 | 7/1994 | Neilson et al. |
| 5,331,975 | 7/1994 | Bonutti . |
| 5,464,437 | 11/1995 | Reid et al. ............................. 607/105 |
| 5,514,153 | 5/1996 | Bonutti ................................. 606/192 |

OTHER PUBLICATIONS

"Design and Thermometry of an Intracavitary Microwave Applicator Suitable For Treatment of Some Vaginal and Rectal Cancers," Ding–Jui Li, M.D. et al., Int. J. Radiation Oncology Biol. Phys., vol. 10, No. 11, pp. 2155–2162, Nov. 1984.

"Cancer Therapy by Hyperthermia and Radiation," edited by C. Streffer et al., proceedings of the 2nd International Symposium, Essen, Jun. 2–4, 1977.

"Induction of Hyperthermia in Deep–Seated Tumors by a Special Microwave Applicator," J. Mendecki et al., proceedings of the 2nd International Symposium, Essen, Jun. 2–4, 1977.

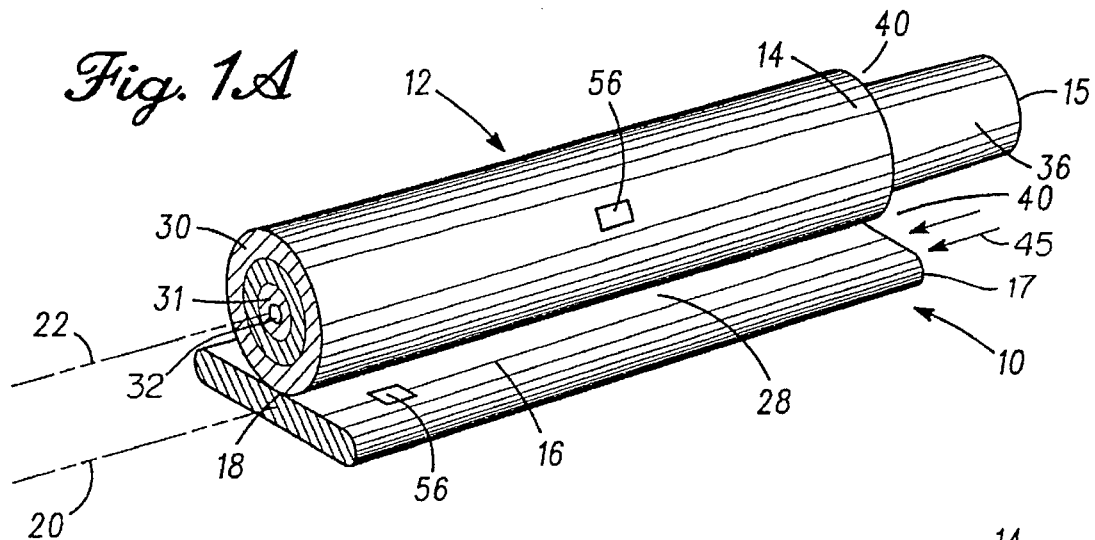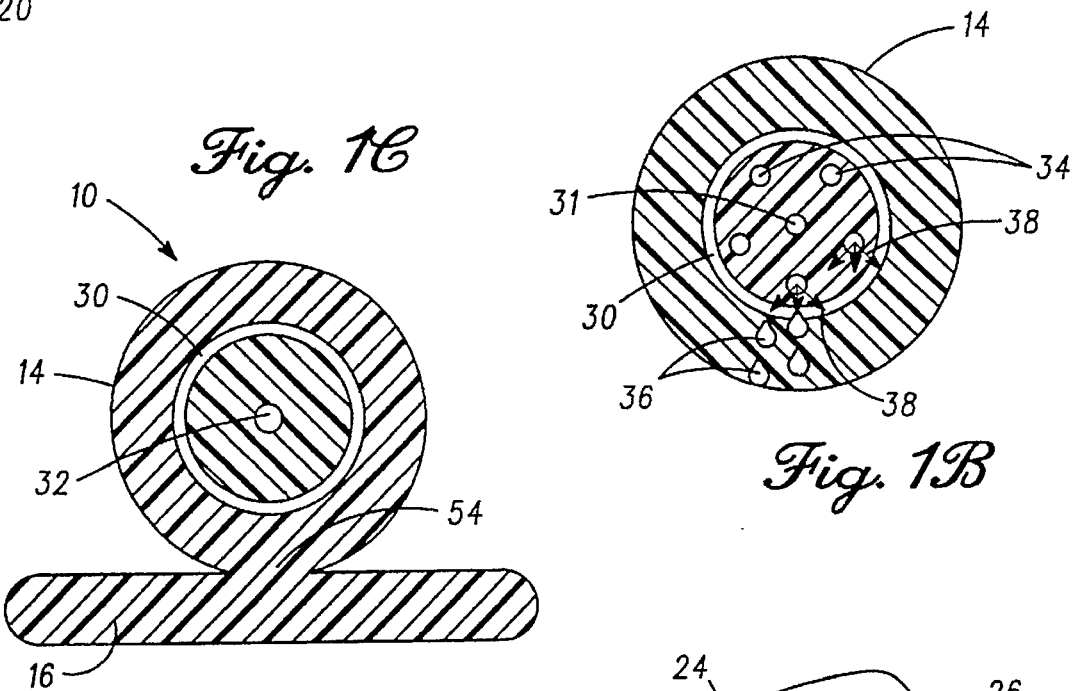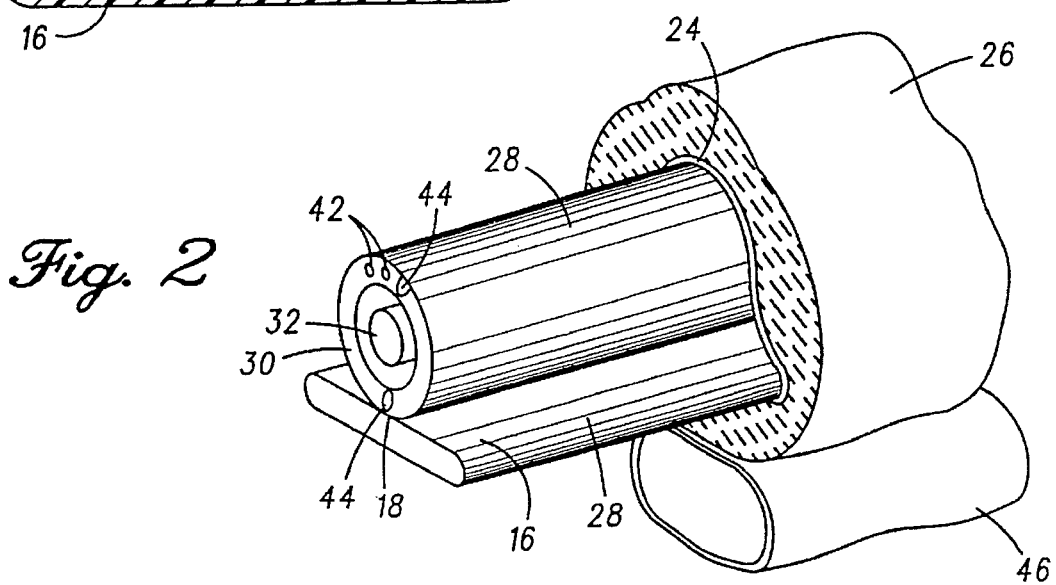

THERMOTHERAPY METHOD WITH TISSUE COOLING

This is a divisional of application Ser. No. 08/291,336, filed on Aug. 17, 1994, now abandoned which is a file wrapper continuation of Ser. No. 07/976,232 filed Nov. 13, 1992, now abandoned.

The Present invention relates generally to an apparatus and method for performing a thermotherapy patient treatment protocol. More particularly, the invention relates to a novel apparatus and method for irradiating and/or heating internal organs, such as the prostate gland, for therapeutic purposes.

Thermotherapy treatment is a relatively new method of treating diseased and/or undesirably enlarged human tissues. Hyperthermia treatment is well known in the art, involving the maintaining of a temperature between about 41.5° through 45° C. Thermotherapy on the other hand usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of larger amounts of energy to the target tissues. At the same time, it is important to shield nontarget tissues from the high thermotherapy temperatures used in the treatment. Providing safe and effective thermotherapy, therefore, requires devices which have further capabilities compared to those which are suitable for hyperthermia.

Though devices and methods for treating benign prostatic hyperplasia have evolved dramatically in recent years, significant improvements have not occurred and such progress is badly needed. As recently as 1983, medical textbooks recommended surgery for removing impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through an incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way, no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating benign prostatic hyperplasia. Researchers began to incorporate heat sources in Foley catheters after discovering that enlarged mammalian tissues responded favorably to increased temperatures. Examples of devices directed to treatment of prostate tissue include U.S. Pat. No. 4,662,383 (Harada), U.S. Pat. No. 4,967,765 (Turner), U.S. Pat. No. 4,662,383 (Sogawa) and German Patent No. DE2407559 C3 (Dreyer). Though these references disclosed structures which embody improvements over the surgical techniques, significant problems still remain unsolved.

Recent research has indicated that enlarged prostate glands are most effectively treated with higher temperatures than previously thought. Complete utilization of this discovery has been tempered by difficulties in shielding rectal wall tissues and other nontarget tissues. While shielding has been addressed in some hyperthermia prior art devices, the higher microwave energy field intensities associated with thermotherapy necessitate structures having further capabilities beyond those suitable for hyperthermia. For example, the symmetrical devices disclosed in the above-referenced patents have generally produced relatively uniform cylindrical energy fields. Even at the lower microwave energy field intensities encountered in hyperthermia treatment, unacceptably high rectal wall temperatures have limited treatment periods and effectiveness. Further, while shielding using radioreflective fluid has been disclosed in the prior art (see for example European Patent Application No. 89,403,199) the location of such radioreflective fluid appears to increase microwave energy field intensity at the bladder and rectal wall. This is contrary to one of the objects of the present invention.

Additionally, many prior art references appear to require traditional rubber anchoring balloons for secure placement and retention of a variety of treatment and bladder drainage devices. Further, these devices are typically flexible and have no stiffening capability for straightening the treatment path for more efficient and consistent treatment.

In addition, efficient and selective cooling of the devices is rarely provided. This increases patient discomfort and increases the likelihood of healthy tissue damage. These problems have necessitated complex and expensive temperature monitoring systems along the urethral wall.

Finally, the symmetrical designs of the above-referenced devices do not allow matching of the microwave energy field to the shape of the abnormally enlarged prostate gland. Ideally, the microwave energy field reaching the tissues should be asymmetric and generally should expose the upper and lateral (side) impinging lobes of the prostate gland to the highest energy. In addition, the field is ideally substantially elliptical such that the energy reaching the sphincters is minimized.

It is therefore an object of the invention to provide an improved apparatus and method suitable for thermotherapy or hyperthermia treatment.

It is a further object of the invention to provide an improved apparatus and method for thermotherapy treatment which provides substantially uniform irradiation of target tissues while effectively shielding nontarget tissues from the temperatures of treatment.

It is another object of the invention to provide an improved thermotherapy device which includes a collimated irradiation of a target zone generally and selective cooling of nontarget tissues.

It is yet a further object of the invention to provide an improved thermotherapy device which is capable of carrying radioreflective and/or radiation absorptive fluid in one or more cooling chambers, while utilizing radiotransparent liquid in one or more cooling passages.

It is yet another object of the invention to provide an improved thermotherapy device which is capable of carrying a sound absorptive or reflective substance in one or more chambers, while utilizing a sound transparent substance in at least one other passage.

It is still another object of the invention to provide an improved thermotherapy device which is capable of carrying a light absorptive or reflective substance in one or more chambers, while utilizing a light transparent substance in at least one other passage.

It is yet an additional object of the invention to provide a novel thermotherapy device having at least one chamber lined with a substance which is reflective or absorptive to light, sound or microwaves.

It is still an additional object of the invention to provide a novel thermotherapy device having two or more chambers wherein a chamber located adjacent to the target tissue can be maintained at higher temperatures than the one or more chambers adjacent nontarget tissues.

It is a still further object of the invention to provide an improved method and apparatus for thermotherapy treatment which substantially straightens the tissue treatment region for more consistent and effective treatment of the desired tissue.

It is still an additional object of the invention to provide an improved thermotherapy device which reduces tissue damage and discomfort by providing more effective cooling to nontarget tissues.

It is yet an additional object of the invention to provide an apparatus and method for remotely sensing nontarget tissue temperatures by monitoring cooling substance temperatures.

It is yet another object of the invention to provide a novel thermotherapy apparatus which can be retained in a selectable treatment position with one or more extended, expandable balloons.

It is still a further object of the invention to provide a novel thermotherapy apparatus which can be retained in a selectable treatment position with one or more selectively extendable and expandable balloons.

It is an additional object of the invention to provide an improved thermotherapy apparatus having one or more extended, expandable balloons in combination with a conventional anchor balloon for increased anchoring forces.

It is yet a further object of the invention to provide a novel thermotherapy apparatus which includes energy means (including, but not limited to, microwave, ultrasound or laser means) in combination with one or more extended, expandable balloons.

It is still a further object of the invention to provide an improved thermotherapy device which substantially conforms to, and therefore can more effectively treat, an asymmetrically enlarged mammalian organ.

It is an additional object of the invention to provide an improved thermotherapy device which includes an antenna or energy sources which produce a substantially elliptical energy output field, thus minimizing energy reaching the rectal wall in benign prostatic hyperplasia thermotherapy treatment.

It is still a further object of the invention to provide an improved thermotherapy apparatus which produces an energy field shaped in accordance with the enlarged mammalian gland to be treated.

It is still an additional object of the invention to provide a remote temperature sensing method using input and output cooling fluid temperatures to predict tissue temperatures.

It is yet a further object of the invention to provide an improved transrectal temperature and position sensing device.

Other advantages and features of the invention will become apparent from the following detailed description and claims and also in the drawings described hereinbelow.

BRIEF DESCRIPTION OF THE DRAWINGS

FIG. 1A illustrates an isometric view of the thermotherapy device constructed in accordance with one form of the invention; FIG. 1B shows a partial end view of the primary cooling lumen; and FIG. 1C illustrates an end view of the thermotherapy device;

FIG. 2 shows an isometric view of a thermotherapy device as it is inserted into the prostate via the urethra;

DETAILED DESCRIPTION OF THE PREFERRED EMBODIMENT

Figure 3A:
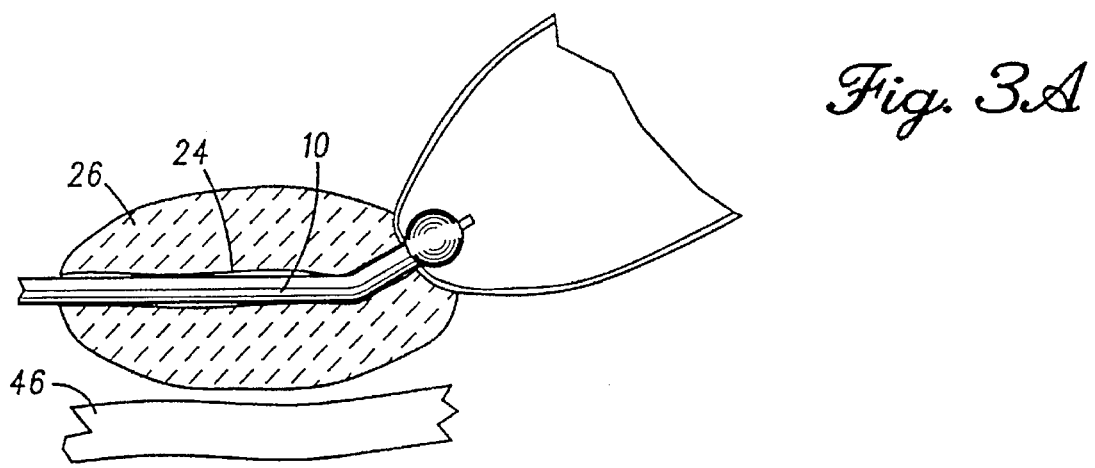
FIG. 3A illustrates the appearance of a naturally curved prostate gland and FIG. 3B illustrates a prostate gland straightened by a thermotherapy device constructed in accordance with the invention.

Referring now to the figures and more particularly to FIG. 1A, a thermotherapy device constructed in accordance with the invention is indicated generally at 10. Throughout the application when referring to "thermotherapy," this terminology shall be meant to include both thermotherapy treatment as well as hyperthermia treatment unless specifically stated to exclude one therapy. An applicator portion 12 of the thermotherapy device 10 includes a primary cooling lumen 14 and a secondary cooling lumen 16. In the preferred form of this invention, "lumen" shall be used to refer to an inflatable and substantially nondistensible structure. The primary cooling lumen 14 and the secondary cooling lumen 16 are disposed adjacent to one another (and can be connected) at perimeter 18 so that their longitudinal axes 22 and 20, respectively, are substantially parallel.

Figure 3B:
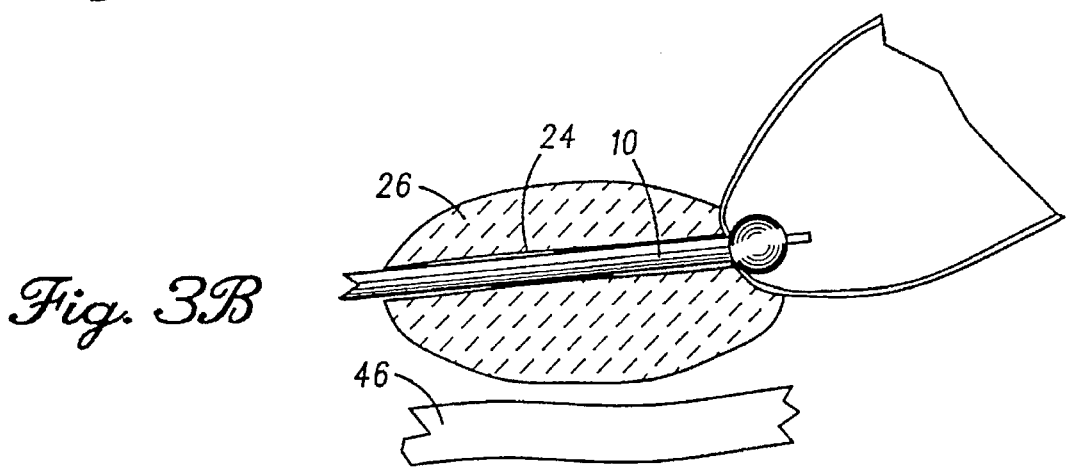
Figure 4:
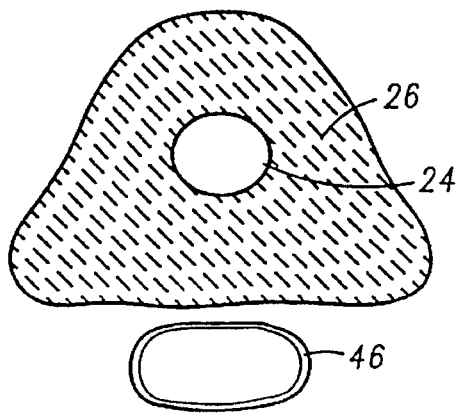
FIG. 4 shows a cross-sectional view of a normal prostate gland, urethra and rectum.

The primary cooling lumen 14 and the secondary cooling lumen 16 can be comprised of a variety of materials including extruded plastics, but are preferably fabricated from a conventional material such as polyethylene terephthalate. This material should preferably have properties resulting in the lumens 14 and 16 being substantially nondistensible, and therefore become substantially rigid when inflated with fluid (liquid or gas) by input into input ends 15 and 17 of the lumens 14 and 16. This rigidity gives rise to several features including the ability to straighten the body passage and surrounding organs into which it is inserted. A nonlimiting example of this feature of the invention shown in FIGS. 2, 3A and 3B is the straightening of the urethra 24 and prostate gland 26 in the thermotherapy treatment of benign prostatic hyperplasia. The lumens can be constructed in a segmented manner as shown in FIG. 3B in phantom to allow selective extension and expansion of the lumens.

As shown in FIG. 3A, the urethra 24 in a normal prostate gland 26 exhibits a curved portion having an angle of approximately 30 degrees. This curved portion of the prostate gland 26 is straightened to the configuration shown in FIG. 3B when the secondary cooling lumen 16 is pressurized to about 30 pounds per square inch with fluid. This straightening action permits treatment of a well-defined geometry, providing a more effective treatment of the prostate gland 26. Such a symmetrical shape allows use of a more predictable energy treatment field. Further, this element of the invention enables the thermotherapy device 10 to be securely anchored by friction along an extended longitudinal expanse of the walls 28 of the thermotherapy device 10, rather than requiring an anchoring balloon along a narrow length or unstable position, such as those needed for securing prior art devices within body passages. It will be obvious, however, to one skilled in the art that a conventional anchoring balloon can be used in conjunction with the novel device disclosed herein to provide additional anchoring force.

In the preferred embodiment illustrated in FIGS. 1A, 1B and 1C, a flexible plastic tubing 30 is disposed within the primary cooling lumen 14. An energy source 31 such as a microwave antenna 32 is inserted into the plastic tubing 30. Multiple holes 34 are provided at the outlet end of the plastic tubing 30 (see FIG. 1B). These holes 34 enable fluid communication between the interior of the plastic tubing 30 and the interior of the primary lumen 14. Cooling fluid 36 can be pumped through the interior of the plastic tubing 30, whereupon it exits through the holes 34 and enters the primary lumen 14 along flow paths 38, for example (see FIG. 1B).

A number of alternative cooling methods can be utilized with this structure. For example, the cooling fluid 36 entering the primary lumen 14 can be allowed to travel the full length of the primary lumen 14 and back the full length again whereupon it exits through the primary lumen outlet 40, as shown in FIG. 1A. In this embodiment, a separate cooling fluid reservoir and pump (not shown) are utilized to circulate water to the secondary cooling lumen 16. This embodiment allows the secondary cooling lumen 16 to be kept at a significantly lower temperature (or different temperature) than the primary cooling lumen 14.

Alternatively, water entering the primary cooling lumen 14 can be allowed to enter the secondary cooling lumen 16 through a series of holes 42 or a slot 44 (see FIG. 2), or other such openings, disposed along the adjacent perimeter 18 of the primary cooling lumen 14 and the secondary cooling lumen 16. This equalizes the temperature in the two lumens 14 and 16 and provides uniform cooling to the tissues within which the thermotherapy device 10 is inserted.

In another embodiment of the invention, cooling fluid 36 can be pumped first into the secondary cooling lumen 16 as indicated by arrows 45 in FIG. 1A. The cooling fluid 36 can then flow into the primary cooling lumen 14 and the plastic tubing 30 through holes 42 or a slot 44 as shown in FIG. 2.

Various pressures and flow volumes of the cooling fluid 36 can be provided to the thermotherapy device 10. In the treatment of benign prostatic hyperplasia, experiments have shown that exceptional cooling can be provided from applying pressures of 30 to 265 pounds per square inch at circulating volumes of 100 to 100 milliliters per minute. It will be obvious to one skilled in the art that different cooling methods, cooling fluids and cooling fluid volumes and pressures can be utilized effectively. Further, it will be obvious to one skilled in the art that heat or radiation sources other than the microwave antenna 32 described for energy source 31 can be equally suitable for proposed treatments (thermotherapy or hyperthermia, though for the purposes of determining the scope of the claims, "thermotherapy" is considered to include hyperthermia treatment). For example, an ultrasound transducer can be used to deliver the radiant energy as the energy source 31. Alternatively, a laser light guide such as the structure disclosed in U.S. Pat. No. 4,878,725 (Hessel, et al.) is a satisfactory energy source 31 when used in conjunction with a laser-transparent lumen material.

The asymmetric structure of the thermotherapy device 10 provides significant improvements over the substantially symmetric devices. As a nonlimiting example, use of the improved thermotherapy device 10 for the treatment of benign prostatic hyperplasia will be described and shown herein.

Referring to the figures, and more particularly to FIG. 2, the thermotherapy device 10 is shown inserted transurethrally into the human prostate gland 26. As shown in FIGS. 2–7, the rectal wall 46 can be located close to the urethra 24 as the device 10 passes through the prostate gland 26.

High temperatures in the rectal wall 46 can be caused by microwave treatment of benign prostatic hyperplasia and can severely limit the duration and effectiveness of the treatment. As discussed previously, thermotherapy requires higher temperatures generally to be maintained at the abnormal tissue compared to conventional hyperthermia treatments. Accordingly, shielding of the rectal wall 46 is even more critical than when performing a hyperthermia treatment.

Figure 5:
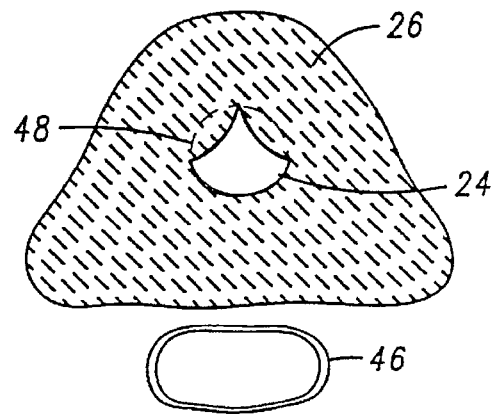
FIG. 5 illustrates a cross-sectional view of a diseased prostate gland impinging upon the urethra.
Figure 6:
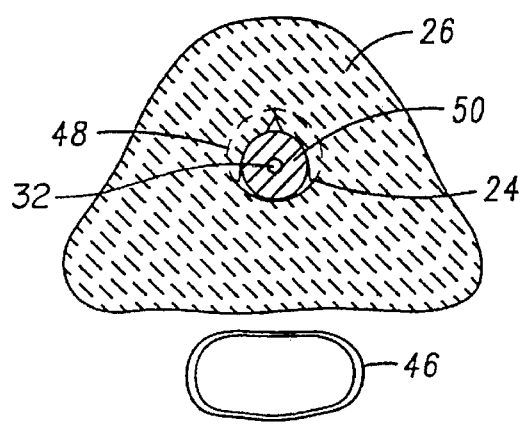
FIG. 6 shows a cross-sectional view of a diseased prostate gland with a traditional treatment device inserted therein.
Figure 7:
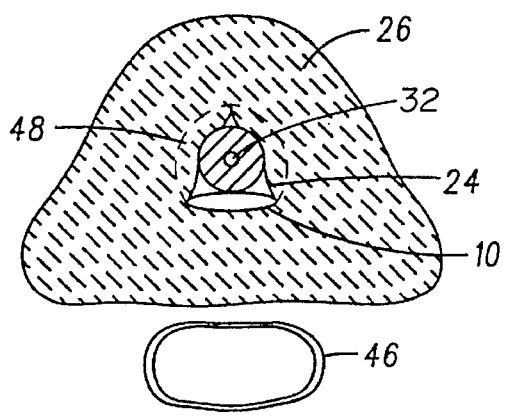
FIG. 7 illustrates a cross-sectional view of a diseased prostate gland with a symmetrical hyperthermia device inserted therein.

Further, as shown in FIGS. 5–7, the transitional zone 48 of the prostate gland 26 is the primary source of tissue impinging upon the urethra 24. This impingement causes difficult urination due to the restricted diameter of the urethra 24. This can cause serious kidney problems and extreme discomfort. The asymmetric structure of the present invention enables application of the radiation to the prostate gland 26 to be preferentially directed to the diseased tissue (such as, the transitional zone 48 in FIG. 5), giving rise to more effective treatment with thermotherapy, while also preventing tissue damage, such as damage to the rectal wall 46.

As shown in FIG. 6, use of a symmetrical applicator 50 for treatment results in treatment being relatively close to the rectal wall 46. The microwave antenna 32 in the applicator 50 typically produces a cylindrical energy field which is symmetric about the antenna's longitudinal axis. High temperatures for the rectal wall 46 can arise from straightforward application of energy from such a cylindrical source and therefore cause reduction of the duration and effectiveness of the treatment of the transitional zone 48 of the prostate gland 26. As shown in FIG. 7, the asymmetric structure of one embodiment of the thermotherapy device 10 physically shifts the microwave antenna 32 toward the transitional zone 48 and away from the rectal wall 46 by dilating (compressing) the overlying and impinging prostate tissue zone 48 of the prostate gland 26.

Figure 8:
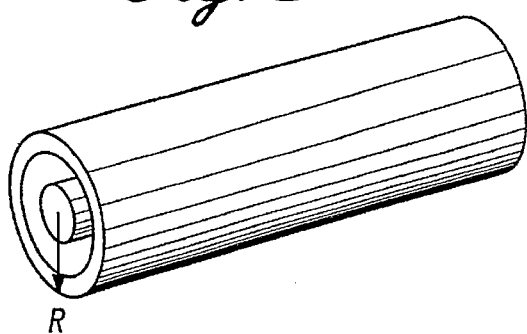
FIG. 8 shows an isometric view of a symmetrical thermotherapy device.

Because microwave field intensity decreases exponentially with distance away from the radiating antenna 32, an exponential decrease in the energy reaching the rectal wall 46 is provided as the secondary cooling lumen 16 (see FIG. 1A) shifts the microwave antenna 32 away from the rectal wall 46. As shown in FIG. 8 in conjunction with Table 1, merely increasing the diameter of the primary cooling lumen 14 only serves to reduce the energy delivered to the transitional zone 48 of the prostate gland 26. Accordingly, thermotherapy treatment effectiveness is reduced with such an approach.

In general, the extent of the microwave field intensity is known to decrease in proportion to the ionic content or properties of the medium. The principle equation governing this concept follows the form:

$$I=(E-\alpha R)/R^2$$

where:

I=microwave field intensity $\alpha$=constant relative to medium (0.5 cm$^{-1}$ for saline; 0.1 cm$^{-1}$ for distilled water)

R=radial distance from the radiating antenna

TABLE 1

| Symmetrical | |
| --- | --- |
| R (cm) | I |
| 0.2 | 24.51 |
| 0.3 | 10.78 |
| 0.4 | 6.00 |
| 0.5 | 3.80 |
| 0.6 | 2.62 |
| 0.7 | 1.90 |

Figure 9:
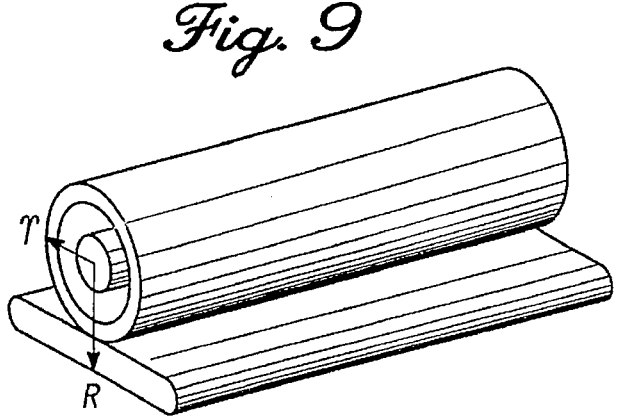
FIG. 9 illustrates an asymmetrical thermotherapy device constructed in accordance with the invention.

The asymmetric structure of the thermotherapy device 10 allows high intensity microwave energy to reach the transitional zone 48 of the prostate gland 26, while substantially preventing high intensity microwave energy from reaching the rectal wall 46. For example, as shown in FIG. 9 and Table 2, increasing the radius of the secondary cooling lumen 16 from two millimeters to four millimeters results in a four-fold reduction in microwave energy reaching the rectal wall 46. Accordingly, more effective thermotherapy treatment of benign prostatic hyperplasia can now be provided with the present invention. Such treatment can be provided without high rectal wall 46 temperatures and attendant damage which severely limits the effectiveness of prior art designs.

TABLE 2

| Asymmetrical | | | | |
| --- | --- | --- | --- | --- |
| R(cm) | r (cm) | I (cm) | I (r) | I(r)/I(R) |
| 0.2 | 0.2 | 24.51 | 24.51 | 1 |
| 0.3 | 0.2 | 10.78 | 24.51 | 2.27 |
| 0.4 | 0.2 | 6.00 | 24.51 | 4.09 |
| 0.5 | 0.2 | 3.80 | 24.51 | 6.45 |
| 0.6 | 0.2 | 2.62 | 24.51 | 9.35 |

In another form of the invention, a radioreflective form of the fluid 36 can be flowed through the secondary cooling lumen 16 to effectively screen the rectal wall 46 from high intensity microwave energy. Another variation on this concept is the use of radiation absorptive fluids 36 in the secondary cooling lumen 16 to screen the rectal wall 46. Another variation is the use of a radioreflective or radiation absorptive substance to form a lining in at least a portion of a cooling chamber to provide the desired screening effect.

In the form of the invention using a laser device as the energy source 31, a light reflective or absorptive fluid or substance can be used in (or on) a cooling chamber to effectively screen the rectal wall 46 from high intensity energy. The form of the invention using an ultrasound type of energy source 31 can utilize a sound reflective or absorptive fluid or substance in (or on) a cooling chamber for high intensity energy screening purposes.

Yet another embodiment of the invention allows interstitial insertion of the thermotherapy device 10 for thermotherapy treatment of tissues which are not located in close proximity to normal body openings or channels. In this embodiment, the thermotherapy device 10 can be inserted into a conventional rigid probe (such as a catheter) that is provided with a pointed insertion tip.

In another form of the invention the primary cooling lumen 14 and/or the secondary cooling lumen 16 can be a single balloon (as shown in FIG. 1C) with a thin liquid barrier 54. The shapes of the lumens 14 and 16 can be modified to provide the desired path length of cooling fluid 36 (and path length of radiation absorber or reflector) seen by energy emanating from the microwave antenna 32 (or other suitable energy source). The cooling fluid 36 can comprise an energy absorber or reflector to enable the clinician to have the ability to construct a desired heating pattern to maximize treatment of disposed tissue and minimize harm to normal tissues.

Figure 10:
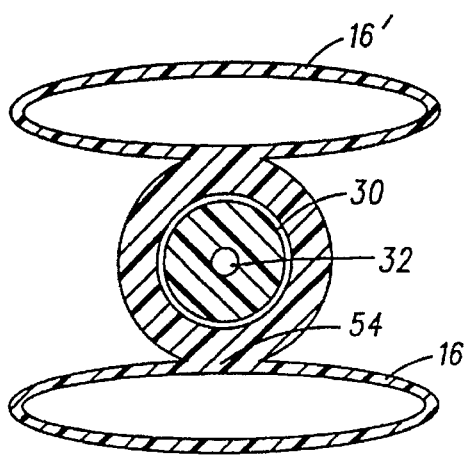
FIG. 10 shows an alternative embodiment of a thermotherapy device including two secondary cooling lumens.

In another form of the invention the device 10 includes two secondary cooling lumens 16 and 16' as shown in FIG. 10. The additional secondary cooling lumen 16' is attached in the same manner as previously disclosed for the first secondary cooling lumen 16. Further, the alternative cooling paths and shielding means for the two lumen device are readily adaptable to the three lumen configuration by one skilled in the art.

This configuration with three lumens adds several advantages over the two lumen configuration disclosed herein. The additional secondary cooling lumen 16 allows greater flexibility in matching the geometry of many prostate glands. In some prostate glands 26, the urethra 24 does not pass through the center of the prostate gland 26, but is off-set in a direction toward non-target tissue. While the two lumen configuration previously disclosed can correct for prostate glands 26 in which the urethra passes closer to the rectal wall 46, the addition of the second secondary cooling lumen 16 enables more efficient and selective treatment of those prostate glands 26 which contain the urethra 24 passing closer to the anterior portion of the prostate gland 26. Without the second secondary cooling lumen 16, the anterior-most portions of the prostate gland 26 can be overheated prior to the rectal wall 46 temperature reaching harmful levels. This can result in injury to the outer capsule of the gland and can lead to complications such as fistula creation between the urethra 24 and the perineum, sepsis and peritonitis. Alternatively, thermotherapy treatment power levels must be decreased for such prostate glands 26 with the uretha 24 passing closer to the anterior portion of the prostate gland 26. In some patients, the location of the urethra can exclude them from treatment with devices other than the three lumen configuration device.

The three lumen configuration of the thermotherapy device 10 will also orient itself within the prostate gland 26 as previously described for other embodiments of the invention. Additionally, the anchoring forces for the thermotherapy device 10 are further improved by the greater surface area provided by the additional secondary cooling lumen 16.

Another embodiment of the present invention utilizes a temperature sensor 56 embedded in a cooling lumen at the tip or along the primary lumen 14 midway along the energy source 31 of the thermotherapy device 10 as shown in FIG. 1A. Alternatively, the temperature of the output temperatures of the cooling fluid 36 have been determined to track the nontarget tissue temperature and can therefore be used to control the treatments.

Figure 11:
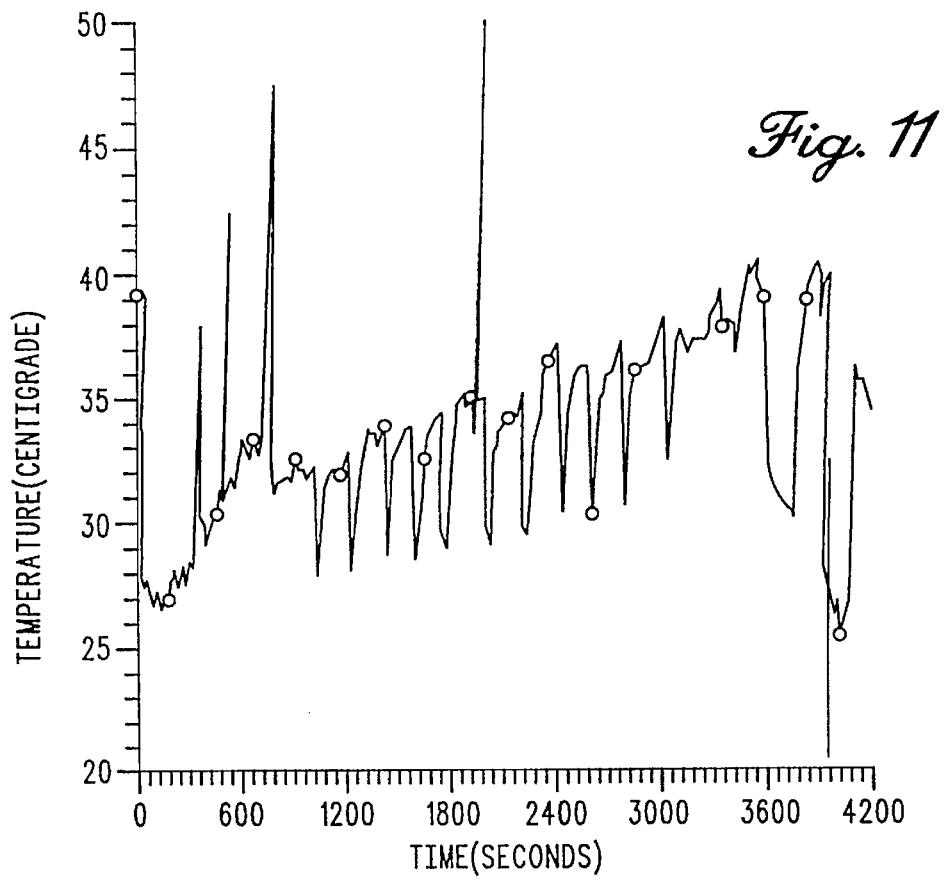
FIG. 11 illustrates temperature readings from a urethral sensor over time.
Figure 12:
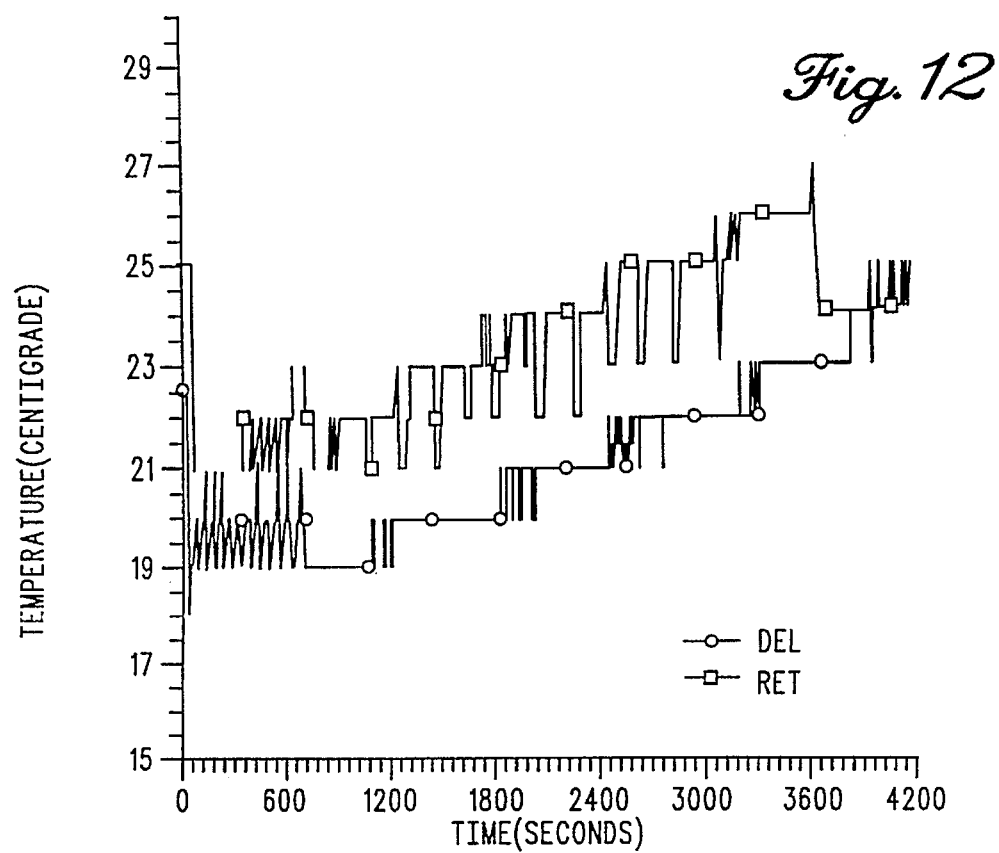
FIG. 12 shows temperature readings from a remote temperature sensor over time.
Figure 13:
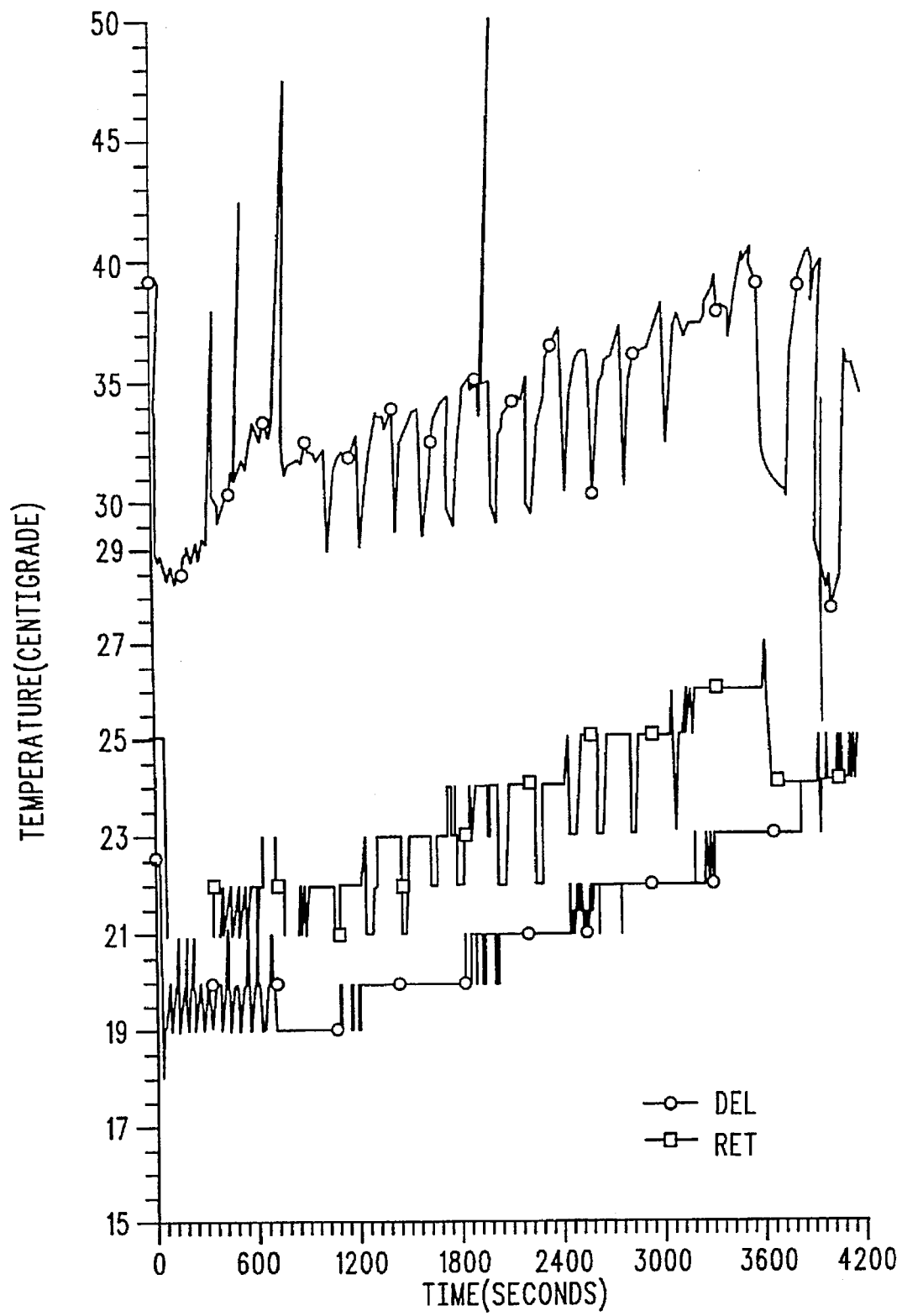
FIG. 13 illustrates a temperature versus time plot produced by superimposing FIGS. 11 and 12.

Referring to FIGS. 11–13, data collected from animal experiments shows a surprisingly good direct correlation between the output temperatures of the cooling fluid 36 and the urethral wall temperatures as monitored by urethral wall temperature sensor. It will be obvious to one skilled in the art that sensing input and output cooling fluid 36 temperature differentials or other remote temperature sensing methods can also satisfactorily control the treatments. While the urethral wall temperature sensor can provide greater sensitivity than a remote sensor, such urethral wall temperature sensors used to monitor temperature immediately adjacent to the microwave antenna 32 require a fiber optic sensor whose temperature does not increase in response to the presence of a strong microwave field. These sensors are very expensive when compared to the temperature sensors which are suitable for use in the remote temperature sensing configuration. Further, a high degree of sensitivity which can be provided by the urethral wall temperature sensor, is not normally needed. Such ultra high sensitivity is not clinically essential because it is not mandatory that the urethral wall be protected against high temperatures. The remote temperature sensing configuration exhibits sufficient sensitivity and can be correlated with patient pain thereby enabling better control.

Figure 14:
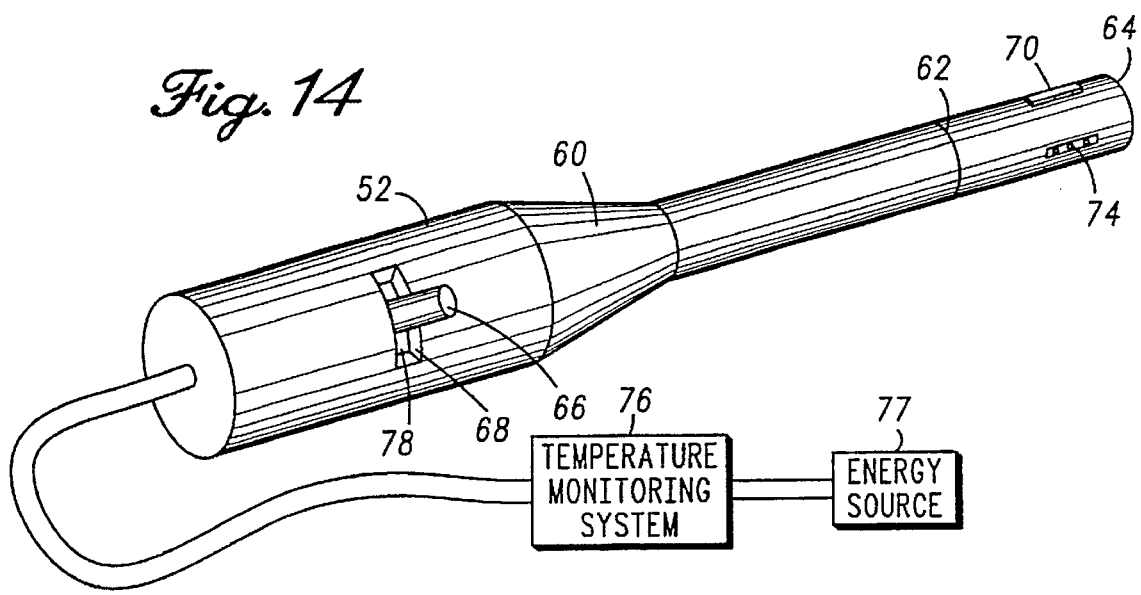
FIG. 14 shows a perspective view of an ultrasound positioning and temperature sensing device constructed in accordance with the invention.
Figure 15:
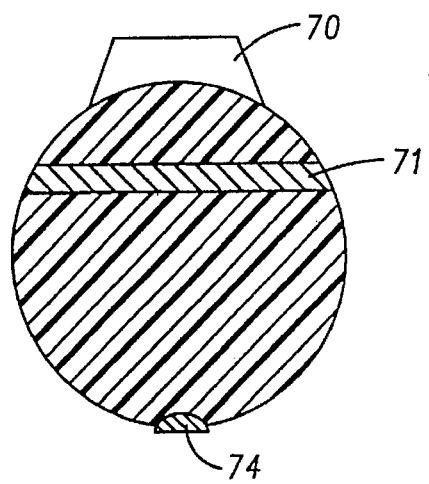
FIG. 15 shows an end view of an alternative embodiment of an ultrasound positioning and temperature sensing device constructed in accordance with the invention.

Referring to FIGS. 14 and 15, another embodiment of the present invention utilizes a transrectal device 52 providing temperature feedback to a temperature monitoring system which controls the microwave energy output of the thermotherapy device 10.

The transrectal device 52 includes a handle portion 60, a rotational joint 62, and a rotating end 64 as shown in FIG. 14. Handle portion 60 of the transrectal device 52 includes a lever 66 which is attached to a portion of rotating end 64 that is disposed within the interior of the handle 60. A slot 68 is provided in the handle portion 60 so that lever 66 can rotate about the perimeter of the handle portion 60. Because lever 66 is attached to a portion of rotating end 64, pivoting the lever 66 in the slot 68 rotates the rotating end 64 coordinately.

Rotating end 64 includes an ultrasound transducer 70, a replaceable array of copper-constantin thermistors 74, and microwave energy shielding material. As shown in FIGS. 14 and 15, the thermistors 74 are offset from the ultrasound transducer 70. Though various angles of offset can be used, preferably the thermistors 74 are one hundred eighty degrees from the ultrasound transducer 70 as shown in FIG. 15. Alternatively (as shown in FIG. 14) the angle of offset can be ninety degrees. This angle of rotation necessitates a slot 68 extending through at least ninety degrees of the perimeter of the handle 60.

Though the transrectal device 52 can be used with other structures, when used in conjunction with the thermotherapy device 10, combined ultrasound positioning of the thermotherapy device 10 and rectal wall temperature monitoring are provided by a single device. Materials can be inserted or applied to the thermotherapy device 10 to render it more visible to ultrasound detection.

The novel structure of the transrectal device 52 minimizes possible effects of microwaves on the ultrasound transducer 70 by shielding the ultrasound transducer 70 from such energy with shielding material 71. Before energy can be applied to the prostate, the portion of the rotating end 64 containing the thermistors 74 must be rotated so it is facing the thermotherapy device 10 in its inserted position in the urethra 24. Feedback from the thermistors 74 is provided by conventional wiring to a temperature monitoring system 76 which turns off the thermotherapy energy source 77 when the desired temperature range is exceeded.

When positioning information is desired, the lever 66 is rotated in the slot 68 so that the ultrasound transducer 70 is facing the thermotherapy device 10 in an inserted position. Lever 66 also includes an electrical switching portion 78 which turns the thermotherapy energy source 77 off when the ultrasound transducer 70 is a position facing the thermotherapy device 10. In this way, the structural integrity of the ultrasound transducer 70 is maintained.

Figure 16:
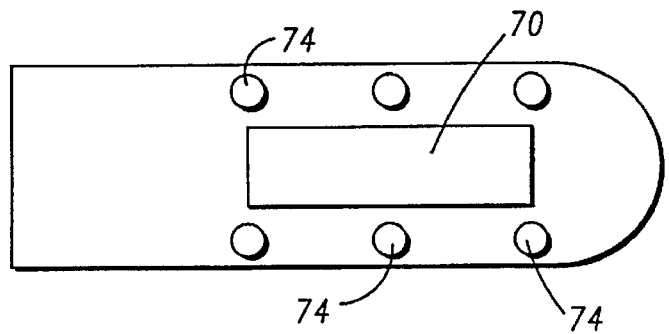
FIG. 16 illustrates another alternative embodiment of an ultrasound positioning and temperature sensing device.

Alternatively, a probe using thermistors 74 and an ultrasound transducer 70 arranged in the manner shown in FIG. 16 can be used to provide temperature and positioning feedback. Further, it will be obvious to one skilled in the art that alternative temperature sensors such as fiber optic-based systems can be readily substituted for the thermistors 74. An alternative to the ultrasound positioning method uses small electrical coils to electronically detect the heating pattern from the thermotherapy device 10. While preferred embodiments have been illustrated and described, it should be understood that changes and modifications can be made therein without departing from the invention in its broader aspects. Various features of the invention are defined in the following claims.

We claim:

1. A method for performing thermotherapy treatment of patient prostate tissue, comprising the steps of:
    inserting a thermotherapy probe in a urethral passageway and said probe having a fluid volume containing portion and an energy source inserted therein for generating radiation to heat the patient prostate tissue by the tissue absorbing the radiation;
    generating a pressurized fluid flow in said probe within said fluid volume confining portion and cooling the energy source by enveloping at least a portion of the energy source to direct said pressurized fluid flow to come into direct contact with and circulate around and over all energy radiating portions of the energy source simultaneously with energy radiation by the energy source thereby preventing thermal damage to the energy source; and
    providing an inflatable nondistensible structure as part of said probe inserted into the urethral passageway and inflating said nondistensible structure with said pressurized fluid flow to cool tissue contacting said nondistensible structure simultaneously with energy radiation by the energy source, thereby controlling pain caused by heating localized areas of the tissue contacting said nondistensible structure, and said nondistensible structure upon inflating causing straightening along a longitudinal axis of the treated patient prostate tissue and said straightening enabling greater uniformity and effectiveness of treatment of the prostate tissue.

2. The method as defined in claim 1, further including the step of remotely indicating tissue temperatures during treatment by sensing the temperature of said fluid.

3. The method as defined in claim 1, further including the step of detecting a position of said probe.

4. A method for performing a prostatic treatment, using a probe capable of straightening a passage in a patient's internal prostatic tissue, comprising the steps of:

inserting a thermotherapy probe having two lumen volume portions one of which is inflatable and substantially nondistensible and upon inflation straightens the patient's internal prostatic tissue passage and an energy source insertable into at least one of said lumen volume portions;

passing liquid through said thermotherapy probe two lumen volume portions after it has been inserted into the prostatic tissue the liquid inflating said nondistensible lumen volume portion; and applying energy from said energy source to heat the prostatic tissues disposed in substantially close proximity to said thermotherapy probe.

5. A method for performing microwave thermotherapy treatment of prostatic tissue, comprising the steps of:

inserting a thermotherapy probe into a urethral passageway and said probe having a fluid volume containing portion and an energy source inserted therein along a lumen of said probe with microwave energy being absorbed by the prostatic tissue; and generating a pressurized fluid flow in said probe Within said fluid volume containing portion to straighten a passage of the prostatic tissue and cooling the energy source by enveloping at least a portion of the energy source to direct said pressurized fluid flow to come into direct contact with and circulate around and over all energy radiating portions of the energy source simultaneously with energy radiation by the energy source, thereby preventing thermal damage to the energy source.

6. The method as defined ha claim 5 wherein said energy source is disposed along a centerline of said probe.

* * * * *

UNITED STATES PATENT AND TRADEMARK OFFICE
CERTIFICATE OF CORRECTION

PATENT NO. : 5,649,973
DATED : Jul. 22, 1997
INVENTOR(S) : Tierney et al.

It is certified that error appears in the above-indentified patent and that said Letters Patent is hereby corrected as shown below:

Title page under Abstract, Line 13: delete second "thereby preventing";

Col. 10, Line 47: delete "confining" and insert --containing--;

Col. 11, Line 13: delete "insertable" and insert --inserted--;

Col. 12, Line 18: delete "ha" and insert --in--.

Signed and Sealed this

Seventh Day of April, 1998

Attest:

BRUCE LEHMAN

Attesting Officer

Commissioner of Patents and Trademarks